US00PP20844P2

(12) United States Plant Patent
Krassenburg

(10) Patent No.: US PP20,844 P2
(45) Date of Patent: Mar. 16, 2010

(54) *IMPATIENS* PLANT NAMED 'SILT WHIT'

(50) Latin Name: *Impatiens walleriana*
Varietal Denomination: Silt Whit

(75) Inventor: Jolanda Krassenburg, Andijk (NL)

(73) Assignee: Goldsmith Seeds Europe, B.V. (NL)

( * ) Notice: Subject to any disclaimer, the term of this patent is extended or adjusted under 35 U.S.C. 154(b) by 0 days.

(21) Appl. No.: 12/316,622

(22) Filed: Dec. 16, 2008

(51) Int. Cl.
*A01H 5/00* (2006.01)

(52) U.S. Cl. ..... Plt./317

(58) Field of Classification Search ..... Plt./317, Plt./319

See application file for complete search history.

*Primary Examiner*—June Hwu
(74) *Attorney, Agent, or Firm*—S. Matthew Edwards

(57) ABSTRACT

A new *Impatiens* plant named 'Silt Whit,' particularly distinguished by large, double-type flowers, white flower color, deep green foliage, compact growth, and tight, low mounding plant habit.

1 Drawing Sheet

Latin name of the genus and species of the plant claimed: *Impatiens walleriana.*

Varietal denomination: 'Silt Whit'.

BACKGROUND OF THE NEW PLANT

The present invention comprises a new *Impatiens,* botanically known as *Impatiens walleriana,* and hereinafter referred to by the variety name 'Silt Whit.'

'Silt Whit' is a product of a planned breeding program. The new cultivar 'Silt Whit' has white flowers of rose-like shape, deep green foliage, and low, mounding, and compact plant habit.

'Silt Whit' originated from a hybridization made in August 2005 in a controlled breeding program in Andijk, Netherlands. The female parent was an unpatented hybrid seedling identified as 'ID03-825-2' with cherry-red colored, single-type flowers.

The male parent of 'Silt Whit' was an unpatented hybrid seedling identified as 'ID03-953-5' with salmon flower color and relatively light green foliage.

The resulting seeds were sown in early November 2005. 'Silt Whit' was selected as one flowering plant within the progeny of the stated cross in December 2005 in a controlled environment in Andijk, Netherlands.

The first act of asexual reproduction of 'Silt Whit' was accomplished when vegetative cuttings were taken from the initial selection in the spring of 2006 in a controlled environment in Andijk, Netherlands.

Horticultural examination of plants grown from cuttings of the plant initiated in the spring of 2006 in Andijk, Netherlands, and continuing thereafter, has demonstrated that the combination of characteristics as herein disclosed for 'Silt Whit' are firmly fixed and are retained through successive generations of asexual reproduction.

'Silt Whit' has not been observed under all possible environmental conditions. The phenotype may vary significantly with variations in environment such as temperature, light intensity and day length.

Plant Breeder's Rights for this cultivar were applied for in Canada on Dec. 24, 2007 and in the European Union on Jul. 21, 2008. 'Silt Whit' has not been made publicly available more than one year prior to the filing of this application.

DESCRIPTION OF THE DRAWINGS

The accompanying photographic drawing shows typical flower and foliage characteristics of 'Silt Whit' with colors being as true as possible with an illustration of this type. The photographic drawing, taken in late May 2008, shows a 15 week old greenhouse grown plant of the new variety.

DETAILED BOTANICAL DESCRIPTION

The measurements were taken in Hillscheid, Germany, mainly in late May 2008 on 14–15 week old plants that were growing on benches in a greenhouse. Culture of these plants had started around February 10 when rooted cuttings were potted in 12 cm pots and grown at moderately warm temperatures, between 15 and 20° C. in daytime.

Color Chart used: Royal Horticultural Society Colour Chart (R.H.S.) 2001.

BRIEF SUMMARY OF INVENTION

The following observations, measurements, and comparisons describe plants grown in a greenhouse in Hillscheid, Germany. The following traits have been repeatedly observed and are determined to be basic characteristics of the new variety. The combination of these characteristics distinguishes this Impatiens as a new and distinct variety.

1. Relatively large, white, double-type flowers
2. Floriferous habit
3. Deep green foliage, ovate to elliptical leaves
4. Small to medium plant size
5. Tight, low, and mounding plant habit
6. Suitable as a patio plant, for containers and even indoors as a flowering potted plant

COMPARISON WITH COMMERCIAL CULTIVARS

'Silt Whit' differs from 'Didi Appleblossom,' U.S. Plant Pat. No. 15,440, in that 'SiltWhit' has a purer white flower color, deeper green foliage, and a more compact and lower plant habit.

Plant:
- *Form, growth and habit.*—Mounding, nearly semi-spherical, tight, under medium sized.
- *Plant height.*—About 8 cm.
- *Plant height* (*inflorescence included*).—About 10 cm.
- *Plant width.*—25–27 cm.
- *Plant size in late summer* (30 *weeks old*).—15–20 cm in height and 30–35 cm in diameter.

Stem:
- *Number of branches.*—16–18.
- *Color of stem.*—Light green, RHS 145B, no anthocyanin.
- *Length of stem.*—8–12 cm.
- *Diameter.*—0.5–0.7 cm.
- *Length of internodes.*—0.5–2.0 cm.
- *Texture.*—Smooth, glabrous.

Foliage:
- *Arrangment.*—Mainly alternate, near tip in whorls.
- *Immature, leaf color, upper surface.*—RHS 137B.
- *Lower surface.*—RHS 138B.
- *Mature, leaf color, upper surface.*—RHS 137B.
- *Lower surface.*—RHS 138B.
- *Length.*—5.5–6.5 cm.
- *Width.*—3.5–4.3 cm.
- *Shape.*—Elliptic to rhomboid.
- *Base shape.*—Acute or attenuate.
- *Apex shape.*—Acuminate.
- *Margin.*—Slightly crenate, ciliate.
- *Texture.*—Dull surface, glabrous, smooth, apart from the veins protruding on the lower side.
- *Color of veins, upper surface.*—Indistinct, RHS 144A.
- *Color of veins, lower surface.*—RHS 144A to 144C at base.

Petiole:
- *Color upper surface.*—RHS 144B.
- *Color lower surface.*—RHS 145B.
- *Length.*—About 1–2 cm.
- *Diameter.*—3 mm.
- *Texture.*—Mainly glabrous.

Inflorescence:
- *Duration of flowering.*—Continuous flowering throughout the summer.
- *Inflorescence type.*—Appear from the upper leaf nodes of the stem, usually a peduncle bears two flowers.
- *Number of flowers and buds per stem.*—Ten or more in various stages of development.

Peduncle:
- *Color.*—RHS 145B to 145C.
- *Length.*—About 2 cm.
- *Diameter.*—2–2.5 mm.
- *Texture.*—Flexible, glabrous.

Pedicel:
- *Color of pedicel.*—RHS 145A to 145B.
- *Length of pedicel.*—1.5–2.3 cm.
- *Diameter of pedicel.*—2 mm.
- *Texture.*—Smooth, glabrous.

Flower:
- *Form.*—Double-type, many petalled.
- *Shape of corolla.*—Round outline, rose-shape.
- *Number of petals.*—About 30–40.
- *Overall color.*—Mainly white, a trace of cream may appear with young flowers in the middle of the flower.
- *Upper surface color.*—Whiter than RHS 155D; only very young petals may appear slightly cream white: RHS N155B.
- *Markings.*—None, apart from a slight greenish hue in the middle of the banner petal: RHS 157B.
- *Lower surface color.*—Whiter than RHS 155D.
- *Diameter of flower.*—4.5–4.8 cm.
- *Depth* (*vertical diameter*) *of flower.*—2.2–2.5 cm.
- *Fragrance.*—None.
- *Longevity.*—Flowers last 6–8 days in greenhouse.
- *Rain tolerance.*—Due to the tight double flower-type somewhat susceptible to botrytis mould; flower quality will be improved if plants are placed under rain protection.

Petals:
- *Shape.*—Banner petal cordate, lateral and lower petals obovate.
- *Apex shape.*—Emarginate for the top petal, rounded for the other ones.
- *Base.*—Mostly acute, rounded for the top petal.
- *Margin.*—Entire.
- *Size of outer petals* (*inner petals are diminishing in size*).—
- *Size of top petal.*—Length: 1.8 cm. Width: 3.0 cm.
- *Size of lateral petals.*—Length: 2.2 cm. Width: 1.8–2.0 cm.
- *Size of lower petals.*—Length: 2.2–2.4 cm. Width: 2.1–2.2 cm.
- *Petal texture.*—Glabrous, smooth.

Spur:
- *Shape.*—Elongate, slating downwards.
- *Color.*—Pale green, RHS 145C.
- *Length.*—Approximately 3.5 cm.
- *Diameter.*—2 mm, thinner towards tip.

Bud (just before opening):
- *Shape.*—Ovoid.
- *Color.*—White, RHS 155D to RHS N155D.
- *Length.*—1.8 cm.
- *Diameter.*—1.5–1.7 cm.

Calyx:
- *Number of sepals.*—5, one of which is transformed into a spur.
- *Sepal shape.*—The largest one with the underside of the banner petal, lateral sepal narrow and lanceolate, lower sepals fused, ovate, and bearing the spur.
- *Apex shape.*—Acute or acuminate.
- *Base shape.*—Rounded.
- *Margins.*—Entire.
- *Color of lateral sepals.*—Medium green, RHS 143B.
- *Color of lower sepals.*—Pale green, RHS 145D to 157A.
- *Length of lateral sepals.*—0.4 cm.
- *Width of lateral sepals.*—0.15 cm.
- *Length of lower sepals.*—1.3 cm.
- *Width of lower sepals.*—0.7 cm.
- *Texture.*—Most parts film-like, and semi-transparent, glabrous.

Reproductive organs: Usually none, only occasionally in rudimental form, as all stamen are transformed into petals.
- *Fertility/seed set.*—Infertile, no seed set observed.

Disease/pest resistance: No particular disease resistance or susceptibility has not been observed on this hybrid.

What is claimed is:

1. A new and distinct variety of *Impatiens* plant named 'Silt Whit,' substantially as illustrated and described herein.

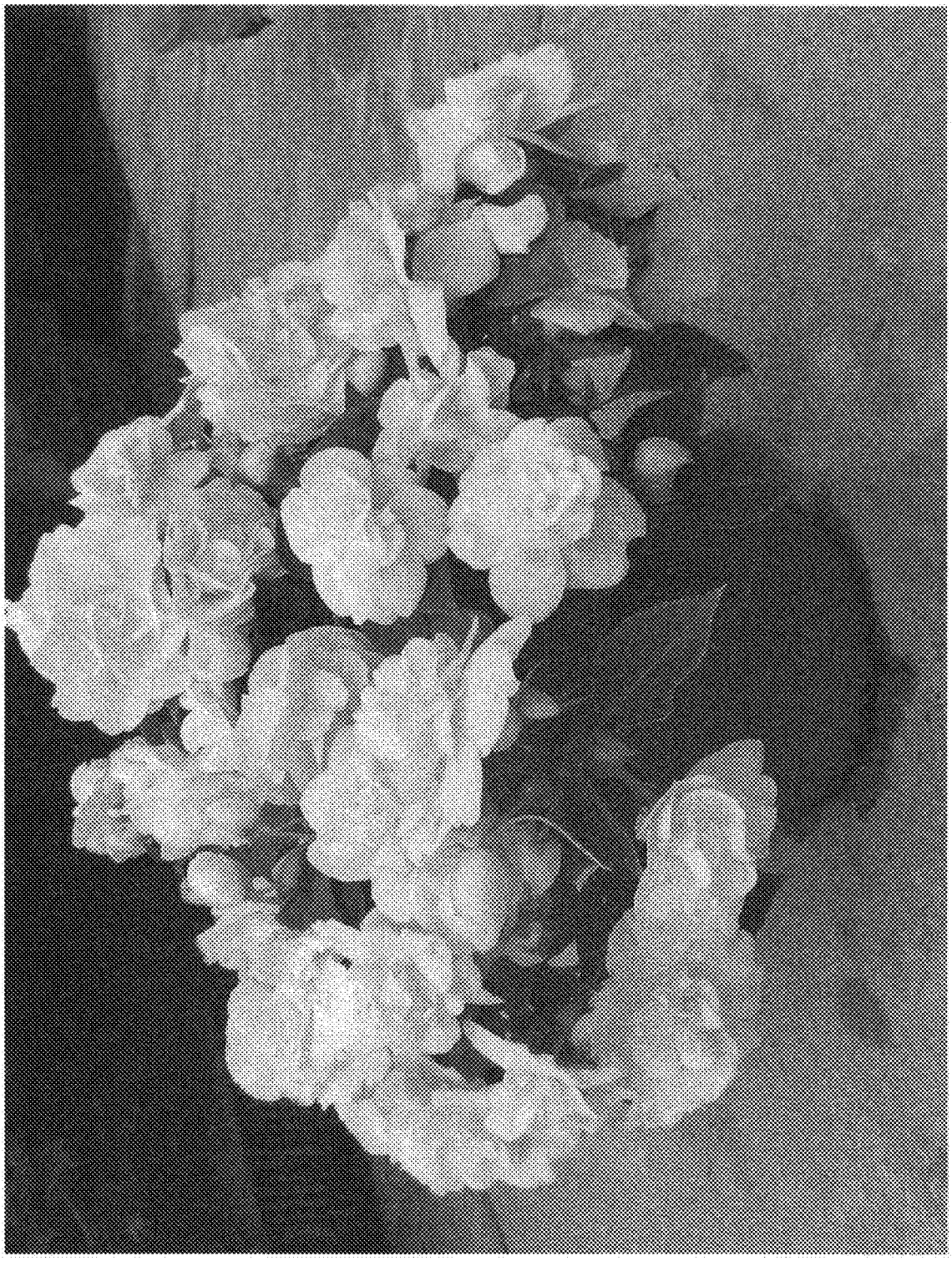

* * * * *